(12) United States Patent
Mei

(10) Patent No.: US 9,745,260 B2
(45) Date of Patent: Aug. 29, 2017

(54) METHOD FOR PURIFYING ACRYLAMIDE ALKYL SULFONIC ACID

(71) Applicant: Longyi Mei, Nanjing, Jiangsu Province (CN)

(72) Inventor: Longyuan Mei, Anhui Province (CN)

(73) Assignee: Longyi Mei, Jiangsu Province (CN)

( * ) Notice: Subject to any disclaimer, the term of this patent is extended or adjusted under 35 U.S.C. 154(b) by 0 days.

(21) Appl. No.: 14/896,387

(22) PCT Filed: Feb. 11, 2014

(86) PCT No.: PCT/CN2014/071948
§ 371 (c)(1),
(2) Date: Dec. 6, 2015

(87) PCT Pub. No.: WO2014/194690
PCT Pub. Date: Dec. 11, 2014

(65) Prior Publication Data
US 2016/0137596 A1    May 19, 2016

(30) Foreign Application Priority Data
Jun. 6, 2013  (CN) .......................... 2013 1 0223515

(51) Int. Cl.
*C07C 303/44* (2006.01)
*C07C 309/15* (2006.01)

(52) U.S. Cl.
CPC .......... *C07C 303/44* (2013.01); *C07C 309/15* (2013.01)

(58) Field of Classification Search
None
See application file for complete search history.

(56) References Cited

U.S. PATENT DOCUMENTS

| | | | |
|---|---|---|---|
| 4,337,215 A | 6/1982 | Doi et al. | |
| 4,650,614 A | 3/1987 | Jevne et al. | |
| 6,331,647 B1 * | 12/2001 | Quinn ................... | C07C 303/44 562/105 |
| 2013/0137893 A1 * | 5/2013 | Ebel ...................... | C07C 303/22 562/105 |

FOREIGN PATENT DOCUMENTS

| | | |
|---|---|---|
| CN | 102952049 | 3/2013 |
| CN | 103044295 | 4/2013 |
| CN | 103086929 | 5/2013 |
| CN | 103254102 | 8/2013 |

OTHER PUBLICATIONS

First Office Action dated Nov. 26, 2013 for CN Application No. 201310223515.3.
Second Office Action dated Apr. 24, 2014 for CN Application No. 201310223515.3.
Notification to Grant Patent Right for Invention dated Jul. 15, 2015 for CN Application No. 201310223515.3.
International Search Report completed May 6, 2014 for PCT/CN2014/071948.
English translation of the Written Opinion of the International Searching Authority mailed May 14, 2014 for PCT/CN2014/071948.
International Preliminary Report on Patentability issued Dec. 8, 2015 for PCT/CN2014/071948.

* cited by examiner

*Primary Examiner* — Yate K Cutliff
(74) *Attorney, Agent, or Firm* — Fleit Gibbons Gutman Bongini & Bianco PL; Paul D. Bianco; Katharine Wong Davis

(57) ABSTRACT

A method for purifying acrylamide alkyl sulfonic acid comprises: (1) making a material A evenly mixed and contacted with a solvent C, an amount of the material A exceeding a solubility of the material A in the solvent C under the condition where the material A is located, therefore the material A is not completely dissolved by the solvent C; (2) keeping the material A even mixed and contacted with the solvent C for at least 5 minutes; (3) performing a solid-liquid separation to obtain a solid, namely, a purified product B with impurities reduced. In the purifying method according to the invention, the material does not need to be completely dissolved, therefore less solvent is used, and the steps of dissolving the material by increasing temperature, separating out by decreasing temperature or removing the solvent are eliminated, so cost is reduced, efficiency is improved, and operations are simplified.

14 Claims, No Drawings

METHOD FOR PURIFYING ACRYLAMIDE ALKYL SULFONIC ACID

TECHNICAL FIELD

The present invention relates to a purifying method, and particularly to a method for purifying acrylamide alkyl sulfonic acid.

BACKGROUND ART

Acrylamide alkyl sulfonic acid and analogues thereof, mainly as a co-monomer and homo-monomer, are widely used in many industries. In some situations where very high degree of polymerization is demanded, the product directly synthesized may still need to be refined to further improve the quality. Many documents, e.g. U.S. Pat. No. 4,337,215, and actual productions relate to the recrystallization purification of acrylamide alkyl sulfonic acid. But the solid added is completely dissolved in all of these refining processes in the prior art, for example, the solid is completely dissolved by increasing the temperature, and then the solid is re-separated out through the methods such as reducing the solvent by decreasing the temperature of the system or by evaporation, rather than intending to use significantly excessive solid. Moreover, all of these methods mainly use organic solvents, such as acetic acid or acetic acid added with a small amount of water, while it is hard to directly use pure water. The advantage of these methods is that the refined product obtained has very good quality, but the disadvantages are high cost, low efficiency, and complex process, etc.

DISCLOSURE OF THE INVENTION

The technical problem to be solved by the present invention is to provide a method for purifying acrylamide alkyl sulfonic acid, which has low cost, high efficiency, and simple and easy operations.

A method for purifying acrylamide alkyl sulfonic acid comprises the steps of:

(1) making a material A evenly mixed and contacted with a solvent C, wherein the material A comprises at least one acrylamide alkyl sulfonic acid compound represented by the following general formula:

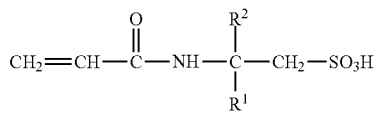

in which $R^1$ and $R^2$ are hydrogen and/or alkyl groups containing 1 to 20 carbons, wherein an amount of the material A exceeds the solubility of the material A in the solvent C under a condition where the material A is located, so that the material A is not completely dissolved by the solvent C;

(2) keeping the material A even mixed and contacted with the solvent C for at least 5 minutes;

(3) performing a solid-liquid separation, wherein because the liquid removed upon separation takes away a portion of impurities dissolved in the liquid, the solid obtained by separation has a reduced amount of impurities, obtaining a purified product B.

In the method for purifying acrylamide alkyl sulfonic acid of the present invention, Step (3) is in either of the following two cases:

1) performing a solid-liquid separation, wherein the solid obtained is not subjected to a drying process, or is subjected to a drying process at or below 50° C., to obtain the purified product B with a solvent C content of greater than or equal to 1%;

performing a solid-liquid separation, wherein the solid obtained is subjected to a drying process at or above 50° C., to obtain the purified product B with a solvent C content of less than 1%.

In the method for purifying acrylamide alkyl sulfonic acid of the present invention, the liquid obtained by the solid-liquid separation is a mother liquor, the solvent C includes the mother liquor obtained in the previous purification or a solution from other sources containing the material A, with the content of the mother liquor or solution of 0~100%.

In the method for purifying acrylamide alkyl sulfonic acid of the present invention, the solvent C comprises at least one selected from the group consisting of the following solvents: water, acid containing 1-8 carbons, amide containing 1-8 carbons, alcohol containing 1-8 carbons, ketone containing 1-8 carbons, ether containing 1-8 carbons, ester containing 1-8 carbons, alkane containing 1-8 carbons, and halogenated hydrocarbon containing 1-8 carbons.

In the method for purifying acrylamide alkyl sulfonic acid of the present invention, the amount of the added material A exceeding the solubility of the material A in the solvent C is 0.01-10 time of the solubility, with the solubility under the condition where the material is located.

In the method for purifying acrylamide alkyl sulfonic acid of the present invention, the temperature of the whole system is controlled between −20° C. and 120° C. during the purifying process, and the temperature is controlled as constant or changed between different temperatures.

In the method for purifying acrylamide alkyl sulfonic acid of the present invention, the material A is contacted with the solvent C for 0.5-48 hours.

In the method for purifying acrylamide alkyl sulfonic acid of the present invention, the amount of the added material A exceeding the solubility of the material A in the solvent C is 0.5-3 time of the solubility, with the solubility under the condition where the material is located; the temperature of the whole system is controlled 0° C. to 25° C. during the purifying process, and the material A is contacted with the solvent C for 0.5-5 hours.

In the method for purifying acrylamide alkyl sulfonic acid of the present invention, the method further comprises adding a polymerization inhibitor until a concentration of the polymerization inhibitor reaches 0 mg/kg~1000 mg/kg and/or feeding oxygen or air, aiming at reducing the risk of polymerization.

The method for purifying acrylamide alkyl sulfonic acid of the present invention comprises steps of:

evenly blending acrylamide methyl sulfonic acid, in which both $R^1$ and $R^2$ are methyl groups in the general formula, with water, and then slowly stirring or allowing the mixture to stand for 0.5-3 hours, with the amount of the added acrylamide methyl sulfonic acid being 1-4 times the solubility in water under an environment where the acrylamide methyl sulfonic acid is located, removing water by filtration or centrifugation to obtain a solid, wherein the purified product obtained is one of the following:

(1) the solid obtained, namely, the product, which is not subjected to a drying process, or subjected to a drying process at or below 50° C., with a water content of greater than or equal to 1%;

(2) the solid obtained, which is subjected to a drying process at or above 50° C. to obtain a product with a water content of less than 1%.

The present invention is different from the prior art in that: in the present invention, after an excessive amount of the material A is in contact with the solvent C for a relatively long period of time, the solid-liquid separation is performed to obtain the solid with a reduced amount of impurities, and a wet product or a dried non-wet product with improved purity is obtained directly. Compared with the conventional method in which the material is dissolved completely, and then re-separating out by decreasing the temperature or removing the solvent to obtain a purified product by separation, since the material does not need to be completely dissolved, less solvent can be used, and the steps of dissolving the material by increasing the temperature, and separating out by decreasing the temperature or removing the solvent and the like are eliminated, so that the cost is reduced, the efficiency is improved, and the operations are simplified.

Below, the method of the present invention is further described in combination with specific examples.

DETAILED DESCRIPTION OF EMBODIMENTS

Example 1

A method for purifying acrylamide alkyl sulfonic acid comprised the following steps:

making a material A evenly mixed and in contact with a solvent C, wherein the material A is acrylamide methyl sulfonic acid with both $R^1$ and $R^2$ being methyl groups in the above-mentioned general formula, the solvent C is water, and the amount of the added material A exceeding the solubility in water under the condition where the material is located is twice the solubility, and the temperature of the whole system is controlled at 10° C. during the purifying process, the temperature is controlled as constant; making the material A in contact with the solvent C for 3 hours; performing a solid-liquid separation in a filtration manner to obtain a wet material of a purified product B, and to obtain the purified dry product B after drying the wet material.

Example 2

A method for purifying acrylamide alkyl sulfonic acid comprised the following steps:

making a material A evenly mixed and contacted with a solvent C, wherein the material A is acrylamide methyl sulfonic acid with both $R^1$ and $R^2$ being methyl groups in the above-mentioned general formula, the solvent C is water, the solvent C comprises a mother liquor of a content of 50% obtained from the previous purification, and the amount of the added material A exceeding the solubility in water under the condition where the material is located is four times of the solubility, the temperature of the whole system is controlled at 0° C.-25° C. during the purifying process, the temperature is controlled as being changed to different temperatures in the range of 0° C.-25° C.; adding a polymerization inhibitor into the system, the concentration as 1000 mg/kg; making the material A contacted with the solvent C for 6 hours; performing a solid-liquid separation in a centrifugation manner to obtain a wet material of a purified product B.

Example 3

A method for purifying acrylamide alkyl sulfonic acid comprised the following steps:

making a material A evenly mixed and contacted with a solvent C, wherein the material A is acrylamide methyl sulfonic acid with both $R^1$ and $R^2$ being methyl groups in the above-mentioned general formula, the solvent C is a mother liquor obtained in the previous purification, and the amount of the added material A exceeding the solubility in water under the condition where the material is located is 0.1 times of the solubility, the temperature of the whole system is controlled at 25° C. during the purifying process, the temperature is controlled as constant; feeding oxygen into the system; making the material A contacted with the solvent C for 0.2 hours; performing a solid-liquid separation in a filtration manner to obtain a wet material of a purified product B, and to obtain the purified dry product B after drying the wet material.

Example 4

A method for purifying acrylamide alkyl sulfonic acid comprised the following steps:

making a material A evenly mixed and contacted with a solvent C, wherein the material A is acrylamide methyl sulfonic acid with both $R^1$ and $R^2$ being methyl groups in the above-mentioned general formula, the solvent C is acetic acid with water of 50%, and the amount of the added material A exceeding the solubility in the solvent C under the condition where the material is located is six times of the solubility, the temperature of the whole system is controlled between −15° C. and 90° C. during the purifying process, the temperature is controlled as being changed to different temperatures in the range of −15° C. to 90° C.; feeding air into the reaction system; making the material A contacted with the solvent C for 1 hour; performing a solid-liquid separation in a filtration manner to obtain a wet material of a purified product B.

Example 5

A method for purifying acrylamide alkyl sulfonic acid comprised the following steps:

making a material A evenly mixed and contacted with a solvent C, wherein the material A is acrylamide methyl sulfonic acid with $R^1$ being an ethyl group and $R^2$ being an alkyl group having 20 carbons in the above-mentioned general formula, the solvent C is alcohol containing 1-8 carbons, the solvent C comprises other solution of a content of 60%, with said other solution containing the material A, the amount of the added material A exceeding the solubility in the solvent C under a condition where the material is located is 5 times of the solubility, the temperature of the whole system is controlled at 45° C. during the purifying process, the temperature is controlled as constant; making the material A contacted with the solvent C for 24 hours; performing a solid-liquid separation in a centrifugation manner to obtain a wet material of a purified product B, and to obtain the purified dry product B after drying the wet material.

Example 6

A method for purifying acrylamide alkyl sulfonic acid comprised the following steps:

making a material A evenly mixed and contacted with a solvent C, wherein the material A is acrylamide methyl sulfonic acid with $R^1$ being an alkyl group containing 15 carbons and $R^2$ being an alkyl group containing 8 carbons in the above-mentioned general formula, the solvent C is acetone, and the amount of the added material A exceeding the solubility in the solvent C under the condition where the material is located is twice the solubility, the temperature of the whole system is controlled at 5° C.-30° C. during the purifying process, the temperature is controlled as being changed to different temperatures in the range of 5° C.-30° C.; adding a polymerization inhibitor into the system, the concentration of the polymerization inhibitor as 50 mg/kg; making the material A contacted with the solvent C for 48 hours; performing a solid-liquid separation in a filtration manner to obtain a wet material of a purified product B.

Example 7

A method for purifying acrylamide alkyl sulfonic acid comprised the following steps:
making a material A evenly mixed and contacted with a solvent C, wherein the material A is acrylamide methyl sulfonic acid with $R^1$ being H and $R^2$ being an alkyl group containing 12 carbons in the above-mentioned general formula, the solvent C is dimethylformamide containing the material A, and the amount of the added material A exceeding the solubility in the solvent C under the condition where the material is located is four times of the solubility, the temperature of the whole system is controlled at 70° C. during the purifying process, the temperature is controlled as constant; making the material A contacted with the solvent C for 5 minutes; performing a solid-liquid separation in a filtration manner to obtain a wet material of a purified product B, and to obtain the purified dry product B after drying the wet material.

Example 8

A method for purifying acrylamide alkyl sulfonic acid comprised the following steps:
making a material A evenly mixed and contacted with a solvent C, wherein the material A is acrylamide methyl sulfonic acid with $R^1$ being an alkyl group containing 15 carbons and $R^2$ being an alkyl group containing 2 carbons in the above-mentioned general formula, the solvent C is a mixture containing water and acetone and methyl ethyl ether and trichloromethane, and the amount of the added material A exceeding the solubility in water under the condition where the material is located is three times of the solubility, the temperature of the whole system is controlled at 10° C. to 30° C. during the purifying process, the temperature is controlled as being changed to different temperatures in the range of 10° C. to 30° C., making the material A contacted with the solvent C for 0.5 hours; performing a solid-liquid separation in a centrifugation manner to obtain a wet material of a purified product B.

Example 9

A method for purifying acrylamide alkyl sulfonic acid comprised the following steps:
making 1500 g of a material A evenly mixed and contacted with 500 g of water, wherein the material A is acrylamide methyl sulfonic acid with both $R^1$ and $R^2$ being methyl groups in the above-mentioned general formula, and the temperature of the whole system is controlled at 15° C. during the purifying process; making the material A contacted with water for 1 hour; performing a solid-liquid separation in a filtration manner to obtain a wet material of a purified product B.

The examples described above are merely to describe the preferred embodiments of the present invention but not to limit the scope of the present invention. For an ordinary person skilled in the art, various alterations and improvements made to the technical solutions of the present invention, without departing from the design spirit of the present invention, should be fallen into the scope of protection defined in the Claims of the present invention.

INDUSTRIAL APPLICABILITY

In the method for purifying acrylamide alkyl sulfonic acid of the present invention, the material does not need to be completely dissolved, and less solvent can be used, and the steps of dissolving the materials by increasing the temperature, and separating out the materials by decreasing the temperature or removing the solvent and the like are eliminated, thus it is much more simplified than the conventional method of recrystallization and purification, and also can obtain the product having better quality than that obtained through the ordinary simple washing method; in particular, due to the property of instability of the double bond of acrylamide alkyl sulfonic acid when heated in water, the solvents such as acetic acid or methanol containing a certain amount of water are mainly used currently in industry for refining, therefore, the cost is high, and the pollution is severe. However, as the process of heating and increasing the temperature and the like are eliminated in the method of the present invention, water can be used directly as solvent for refining, as a result, the cost is greatly reduced, the efficiency is significantly improved, and the operations are considerably simplified; the method according to the present invention is environmentally-friendly and energy-saving, safe and reliable, and has a great market prospect and strong industrial applicability.

The invention claimed is:
1. A method for purifying acrylamide alkyl sulfonic acid, the method comprising steps of:
(a) making a material A evenly mixed and contacted with a solvent C, the material A comprising at least one acrylamide alkyl sulfonic acid compound represented by general formula:

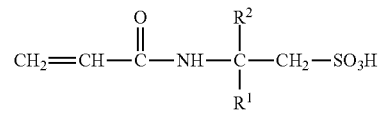

in which $R^1$ and $R^2$ are selected from hydrogen, an alkyl group containing 1 to 20 carbons, and combinations thereof, and an amount of the material A exceeds a solubility of the material A in the solvent C under a condition where the material A is located, so that the material A is partially dissolved by the solvent C;
(b) keeping the material A even mixed and contacted with the solvent C for at least 1 hour, the solvent C selected from the group consisting of water, acid containing 1-8 carbons, amide containing 1-8 carbons, alcohol containing 1-8 carbons mixed in water, ketone containing 1-8 carbons, ether containing 1-8 carbons, ester containing 1-8 carbons, alkane containing 1-8 carbons, halogenated hydrocarbon containing 1-8 carbons, and combinations thereof;

c) performing a solid-liquid separation to obtain a solid, the solid a purified product B, in which the product B is purified material A; and wherein the method does not include steps for dissolving the material A by increasing temperature, re-separating out by decreasing temperature, or removing the solvent.

2. The method for purifying acrylamide alkyl sulfonic acid according to claim 1, wherein Step c) comprises either of:

i) performing the solid-liquid separation, wherein the solid obtained is not subjected to a drying process, or is subjected to a drying process at or below 50° C., to obtain the purified product B with a solvent C content of greater than or equal to 1%; or ii) performing the solid-liquid separation, wherein the solid obtained is subjected to a drying process at or above 50° C., to obtain the purified product B with a solvent C content of less than 1%.

3. The method for purifying acrylamide alkyl sulfonic acid according to claim 2, wherein a liquid obtained from the solid-liquid separation is a mother liquor, and wherein the solvent C comprises a mother liquor obtained in a previous purification or a solution from another source containing the material A, with a content of the mother liquor or the solution 0~100%.

4. The method for purifying acrylamide alkyl sulfonic acid according to claim 1, wherein an amount of the material A exceeding the solubility of the material A in the solvent C is 0.01-10 times the solubility, with the solubility under a condition where the material A is located.

5. The method for purifying acrylamide alkyl sulfonic acid according to claim 4, wherein temperature is controlled between −20° C. and 120° C. during purifying, the temperature controlled as constant or changed between different temperatures.

6. The method for purifying acrylamide alkyl sulfonic acid according to claim 5, wherein the material A is contacted with the solvent C for a period of time between 1 hour and 48 hours.

7. The method for purifying acrylamide alkyl sulfonic acid according to claim 6, wherein the amount of the material A exceeding a solubility of the material A in the solvent C is 0.5-3 times of the solubility, with the solubility under a condition where the material A is located; the temperature is controlled between 0° C. and 25° C. during purifying; and the material A is contacted with the solvent C for 0.5-5 hours.

8. The method for purifying acrylamide alkyl sulfonic acid according to claim 4, further comprising a step of:

adding a polymerization inhibitor until a concentration of the polymerization inhibitor reaches 0 mg/kg~1000 mg/kg; and feeding oxygen or air.

9. The method for purifying acrylamide alkyl sulfonic acid according to claim 8, the method comprising steps of:

evenly blending acrylamide methyl sulfonic acid, in which both $R^1$ and $R^2$ are methyl groups in the general formula, with water to obtain a mixture;

slowly stirring or allowing the mixture to stand for 0.5-3 hours, an amount of the added acrylamide methyl sulfonic acid 1-4 times the solubility of the acrylamide methyl sulfonic acid in water under an environment where the acrylamide methyl sulfonic acid is located; and removing water by filtration or centrifugation to obtain a solid, purified product, wherein the solid, purified product is:

(i) a solid, purified product, which is not subjected to a drying process, or is subjected to a drying process at or below 50° C., having a water content of greater than or equal to 1%; or (ii) a solid, purified product, which is subjected to a drying process at or above 50° C. having a water content of less than 1%.

10. A method for purifying acrylamide alkyl sulfonic acid, the method comprising steps of:

(a) making a material A evenly mixed and contacted with a solvent C, the material A comprising at least one acrylamide alkyl sulfonic acid compound represented by general formula:

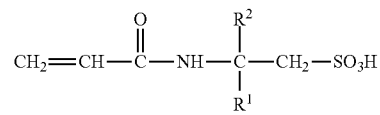

in which $R^1$ and $R^2$ are selected from hydrogen, an alkyl group containing 1 to 20 carbons, and combinations thereof, and an amount of the material A exceeds a solubility of the material A in the solvent C under a condition where the material A is located, so that the material A is partially dissolved by the solvent C;

(b) keeping the material A even mixed and contacted with the solvent C for at least 1 hour, wherein the solvent C selected from the group consisting of water, acid containing 1-8 carbons, amide containing 1-8 carbons, alcohol containing 1-8 carbons mixed with water, ketone containing 1-8 carbons, ether containing 1-8 carbons, ester containing 1-8 carbons, alkane containing 1-8 carbons, halogenated hydrocarbon containing 1-8 carbons, and combinations thereof;

c) performing a solid-liquid separation to obtain a solid, the solid a purified product B, in which the product B is purified material A, wherein a temperature is set and controlled as constant at step (a), at step (b), and at step (c); and wherein the method does not include steps for dissolving the material A by increasing temperature, re-separating out by decreasing temperature, or removing the solvent.

11. The method for purifying acrylamide alkyl sulfonic acid according to claim 10, wherein the temperatures at step (a), at step (b), and at step (c) are set and controlled at equivalent or different temperatures.

12. A method for purifying acrylamide alkyl sulfonic acid, the method comprising steps of:

(a) making a material A evenly mixed and contacted with a solvent C, the material A comprising at least one acrylamide alkyl sulfonic acid compound represented by general formula:

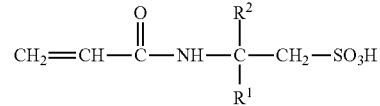

in which $R^1$ and $R^2$ are selected from hydrogen, an alkyl group containing 1 to 20 carbons, and combinations thereof, and an amount of the material A exceeds a solubility of the material A in the solvent C under a condition where the material A is located, so that the material A is partially dissolved by the solvent C;

(b) keeping the material A even mixed and contacted with the solvent C for at least 1 hour, wherein the solvent C is water;

c) performing a solid-liquid separation to obtain a solid, the solid a purified product B, in which the product B is purified material A; and wherein the method does not include steps for dissolving the material A by increasing temperature, re-separating out by decreasing temperature, or removing the solvent.

13. The method for purifying acrylamide alkyl sulfonic acid according to claim 12, wherein a temperature is set and controlled as constant at step (a), at step (b), and at step (c).

14. The method for purifying acrylamide alkyl sulfonic acid according to claim 13, wherein the temperatures at step (a), at step (b), and at step (c) are set and controlled at equivalent or different temperatures.

* * * * *